(12) United States Patent
Brown et al.

(10) Patent No.: US 10,617,333 B2
(45) Date of Patent: Apr. 14, 2020

(54) ACOUSTICALLY PROBED OVER-THE-EAR HEARING ASSESSMENT DEVICES AND METHODS

(71) Applicant: 3M INNOVATIVE PROPERTIES COMPANY, St. Paul, MN (US)

(72) Inventors: James D. Brown, Bloomington, IN (US); Jacob H. Ely, Indianapolis, IN (US); Michael G. Wurm, Waukesha, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 337 days.

(21) Appl. No.: 15/511,484

(22) PCT Filed: Sep. 16, 2015

(86) PCT No.: PCT/US2015/050328
§ 371 (c)(1),
(2) Date: Mar. 15, 2017

(87) PCT Pub. No.: WO2016/044362
PCT Pub. Date: Mar. 24, 2016

(65) Prior Publication Data
US 2017/0245787 A1 Aug. 31, 2017

Related U.S. Application Data

(60) Provisional application No. 62/052,713, filed on Sep. 19, 2014.

(51) Int. Cl.
*A61B 5/00* (2006.01)
*A61B 5/12* (2006.01)
(Continued)

(52) U.S. Cl.
CPC ............ *A61B 5/123* (2013.01); *A61B 5/6803* (2013.01); *A61F 11/14* (2013.01); *H04R 1/1008* (2013.01);
(Continued)

(58) Field of Classification Search
CPC ........... A61B 5/12; A61B 5/121; A61B 5/123; A61B 5/125; A61B 5/6803; A61B 5/6815;
(Continued)

(56) References Cited

U.S. PATENT DOCUMENTS 3,098,307 A 7/1963 Caldwell, Jr.
3,335,720 A 8/1967 Aileo
(Continued)

FOREIGN PATENT DOCUMENTS

AU 1996061949 2/1997
DE 3903246 8/1990
(Continued)

OTHER PUBLICATIONS

International Search Report for PCT International Application No. PCT/US2015/050328, dated Dec. 9, 2015, 4 pages.

*Primary Examiner* — Max F Hindenburg
(74) *Attorney, Agent, or Firm* — Katherine M. Scholz; Dena M. Ehrich

(57) ABSTRACT

An over-the-ear hearing assessment device and a method for evaluating the performance of over-the-ear hearing devices are described. An exemplary over-the-ear hearing assessment device includes an ear cup defining an interior volume and positionable at least partially over the ear of a user. The ear cup includes a shell, a cushion, and an acoustic port extending from an exterior to the interior volume of the ear cup. The acoustic port is sealably engagable with a microphone.

19 Claims, 5 Drawing Sheets

(51) Int. Cl.
  *H04R 1/10*   (2006.01)
  *A61F 11/14*  (2006.01)
  *H04R 3/00*   (2006.01)
  *H04R 29/00*  (2006.01)
  *H04R 1/40*   (2006.01)

(52) U.S. Cl.
  CPC ............ *H04R 1/406* (2013.01); *H04R 3/005* (2013.01); *H04R 29/00* (2013.01); *H04R 29/001* (2013.01); *H04R 2460/15* (2013.01)

(58) Field of Classification Search
  CPC ......... A61F 11/14; H04R 1/10; H04R 1/1008; H04R 1/406
  See application file for complete search history.

(56) References Cited

U.S. PATENT DOCUMENTS

| | | | |
|---|---|---|---|
| 3,729,598 A | 4/1973 | Tegt | |
| 3,968,334 A | 7/1976 | Padilla | |
| 4,060,701 A | 11/1977 | Epley | |
| 4,156,118 A | 5/1979 | Hargrave | |
| 4,299,303 A | 11/1981 | Clark | |
| 4,302,635 A | 11/1981 | Jacobsen | |
| 5,317,273 A | 5/1994 | Hanson | |
| 5,577,511 A | 11/1996 | Killion | |
| 5,632,048 A * | 5/1997 | Mortell | A42B 3/166 2/423 |
| 5,757,930 A | 5/1998 | Seidemann | |
| 5,970,795 A | 10/1999 | Seidemann | |
| 6,151,717 A | 11/2000 | Lindgren | |
| 6,353,938 B1 | 3/2002 | Young | |
| 6,456,199 B1 | 9/2002 | Michael | |
| 6,466,681 B1 * | 10/2002 | Siska, Jr. | H04R 5/0335 381/370 |
| 7,037,274 B2 * | 5/2006 | Thornton | A61B 5/12 600/559 |
| 7,242,778 B2 * | 7/2007 | Csermak | H04R 25/305 381/315 |
| 7,574,917 B2 * | 8/2009 | Von Dach | G01H 15/00 181/135 |
| 7,688,983 B2 | 3/2010 | Voix | |
| 8,249,266 B2 | 8/2012 | Michael | |
| 8,254,587 B2 | 8/2012 | Voix | |
| 8,433,071 B2 | 4/2013 | Latzel | |
| 9,100,745 B2 * | 8/2015 | Oishi | H04R 1/1041 |
| 9,554,733 B2 * | 1/2017 | Henriksen | A61B 5/12 |
| 2002/0076057 A1 | 6/2002 | Voix | |
| 2005/0094824 A1 | 5/2005 | Chuang | |
| 2005/0123146 A1 | 6/2005 | Voix | |
| 2007/0214893 A1 | 9/2007 | Killion | |
| 2008/0011084 A1 | 1/2008 | Dach | |
| 2011/0056299 A1 | 3/2011 | Killion | |
| 2011/0311079 A1 | 12/2011 | Keady | |
| 2012/0217087 A1 | 8/2012 | Ambrose | |
| 2012/0243699 A1 | 9/2012 | Michael | |

FOREIGN PATENT DOCUMENTS

| | | |
|---|---|---|
| EP | 0912075 | 4/1999 |
| EP | 2044807 | 4/2009 |
| EP | 2059067 | 5/2009 |
| JP | 2012244522 | 12/2012 |
| JP | 2013143612 | 7/2013 |
| WO | WO 97/23117 | 6/1997 |
| WO | WO 2003/019982 | 3/2003 |
| WO | WO 2003-099113 | 12/2003 |

* cited by examiner

ACOUSTICALLY PROBED OVER-THE-EAR HEARING ASSESSMENT DEVICES AND METHODS

TECHNICAL FIELD

The present description relates to over-the-ear hearing devices, and methods for evaluating performance of over-the-ear hearing devices.

BACKGROUND

The use of hearing protection devices (HPDs) and noise attenuating devices are well known, and various types of devices have been considered. Such devices include in-ear devices, such as earplugs, and over-the-ear devices, such as ear muffs, ear defenders, etc. Performance of over-the-ear hearing devices has often been evaluated in a laboratory environment. According to one method, an artificial test head or dummy head having artificial flesh and/or artificial ear drums, may be used, and over-the-ear devices may be evaluated by positioning a microphone inside the head near the artificial ear drum and positioning another microphone outside the device. There remains a need for effective evaluation of over-the-ear hearing devices.

SUMMARY

The present description provides an over-the-ear hearing assessment device. An exemplary over-the-ear hearing device includes an ear cup defining an interior volume and configured to be positioned at least partially over the ear of a user. The ear cup includes a shell, a cushion and an acoustic port extending from an exterior to the interior volume of the ear cup. The acoustic port includes a mating feature sealingly engagable with a microphone.

The present description further provides a method of evaluating performance of an over-the-ear device. An exemplary method includes steps of positioning an over-the-ear hearing device in a position of use over at least one ear of a user, the over-the-ear hearing device including an ear cup defining an interior volume and including a shell, a cushion, and an acoustic port extending from an exterior to the interior volume of the ear cup, exposing the hearing protector to at least one test sound; and comparing an interior sound level detected through the acoustic port by a microphone in sealing engagement with the acoustic port and an exterior sound level detected proximate the exterior of the hearing protector.

The present description further provides an over-the-ear hearing device cushion including a cellular foam material defining an opening, an attachment ring attached to the cellular foam material and having a mating feature configured for replaceable attachment to an ear cup, and an acoustic port comprising a tube passing through the cellular material.

The above summary is not intended to describe each disclosed embodiment or every implementation. The Figures and Detailed Description, which follow, more particularly exemplify illustrative embodiments.

BRIEF DESCRIPTION OF DRAWINGS

The present description will be further explained with reference to the appended Figures, wherein like structure is referred to by like numerals throughout the several views, and wherein.

While the above-identified figures set forth various embodiments of the disclosed subject matter, other embodiments are also contemplated. In all cases, this description presents the disclosed subject matter by way of representation and not limitation. It should be understood that numerous other modifications and embodiments can be devised by those skilled in the art which fall within the scope and spirit of the principles of this description.

DETAILED DESCRIPTION

The present description provides an over-the-ear hearing device and a method of evaluating performance of the over-the-ear hearing device. The hearing device includes an acoustic port including a passageway extending from an exterior to an interior volume of the device. The acoustic port allows acoustic access to an interior volume of the device while in a normal position of use to allow an interior sound level to be detected by a microphone sealingly engaged with the acoustic port.

An over-the-ear hearing device according to the present description allows an acoustic assessment to be performed while a device is in a normal position of use, and, for example, allows an assessment to be performed at various times during the life of the hearing device. Over-the-ear devices as described herein overcome deficiencies present in laboratory test methods, for example. While performance of over-the-ear devices may vary over the life of the product or according to a user's personal attributes, over-the-ear devices provided by the present description allow assessment in situ while the device is in a position of use on a user.

Figure 1:
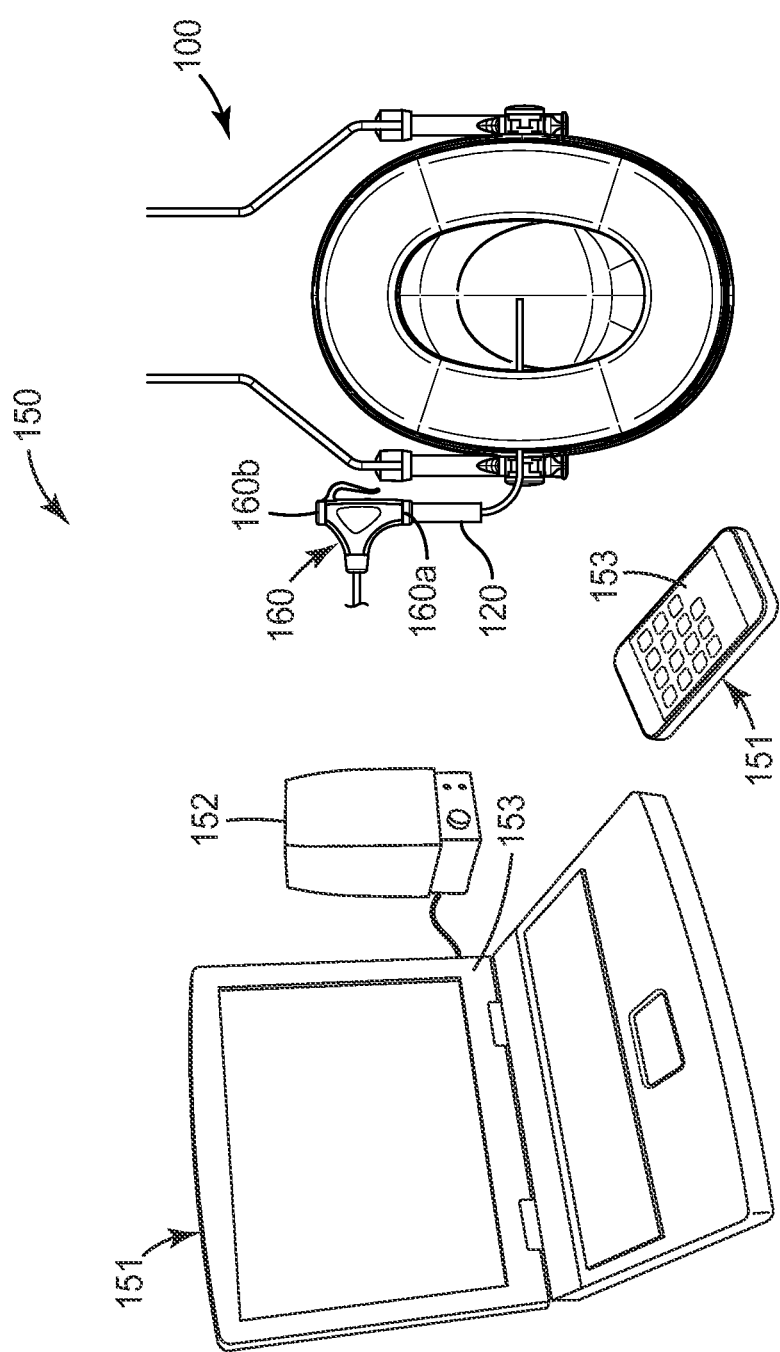
FIG. 1 is a simplified schematic diagram of an exemplary system configured for assessment of an over-the-ear hearing device.

FIG. 1 shows an exemplary over-the-ear hearing protection assessment apparatus 150 for assessing acoustical performance of an over-the-ear hearing device 100, as described herein. Over-the-ear hearing device 100 may be an ear muff, ear defender, communication device, hearing protection device, or other over-the-ear hearing device. As will be described further herein, hearing device 100 includes an acoustic port 120 that extends through hearing device 100 and provides a passageway between an exterior and an interior volume of hearing device 100.

In an exemplary embodiment, apparatus 150 includes a controller 151, operatively connected to a broadband reference sound source 152, and a user interface 153. Sound source 152 is configured to generate a sound having a frequency range between 100 Hz to about 10000 Hz, and includes such octave bands of 125 Hz, 250 Hz, 500 Hz, 1000 Hz, 2000 Hz, 4000 Hz, and 8000 Hz, for example. Controller 151 is configured to provide a signal to control operation of sound source 152. In an exemplary embodiment, controller 151 is a computing device having a processor, such as a personal computer, smart phone, hand held device, dedicated controller, or other suitable controller as known in the art. One or more user interface components 153 are operatively connected to controller 151 such that a user may operate apparatus 150, and may include any suitable user interface components for a user to provide input and receive output, such as a keypad, keyboard, touch screen, voice input, speaker, display, connection, other suitable user interface components as known in the art, and combinations thereof. Controller 151, sound source 152, user interface components 153, and/or other components of apparatus 100 may be housed separately or housed together as a "standalone" over-the-ear hearing protection assessment apparatus, for example.

Apparatus 150 includes one or more microphones 160 operatively connected to controller 151. In an exemplary embodiment, a first microphone 160a is positioned in fluid communication with acoustic port 120 of over-the-ear hearing device 100 to detect an interior sound level and a second microphone 160b is positioned to detect an exterior sound level proximate over-the-ear hearing device 100. First and second microphones 160a, 160b, may be separately mounted microphones or may share a common housing, or otherwise be joined and/or mounted together, for example in back-to-back relationship relative to one another such that first microphone 160a measures a sound level at an interior volume of over-the-ear device and second microphone 160b measures an external sound level proximate over-the-ear device 100 while device 100 is in a position of use at least partially over an ear of a user. In another exemplary embodiment, first microphone 160a may first measure an interior sound level, and subsequently measure an exterior sound level after being repositioned, or vice versa, such that both interior and exterior sound levels may be obtained with a single microphone. First and/or second microphones 160a, 160b thus allow interior and exterior sound pressure levels to be obtained while device 100 is in a position of use such that acoustical performance of over-the-ear device 100 may be considered by comparing the interior and exterior sound levels.

Apparatus 150 is useful in assessing acoustic performance of over-the-ear hearing devices. Over-the-ear hearing devices providing a level of hearing protection as described herein may be assessed to obtain a Personal Attenuation Rating (PAR), for example. A PAR is a single number value that represents the individual attenuation that a user obtains in a Real-Ear Attenuation at Threshold (REAT) test, for example, that may be performed as known in the art, and is representative of an actual attenuation obtained by a user of a particular over-the-ear hearing device. A user's PAR may be obtained from a measured noise reduction in which an interior sound level and exterior sound level are compared. Exemplary over-the-ear hearing devices as described further herein allow consistent and repeatable detection of interior and exterior sound pressure levels while the device is worn by a user and facilitate determination of a user's Personal Attenuation Rating (PAR) for a particular hearing device.

Figure 2A:
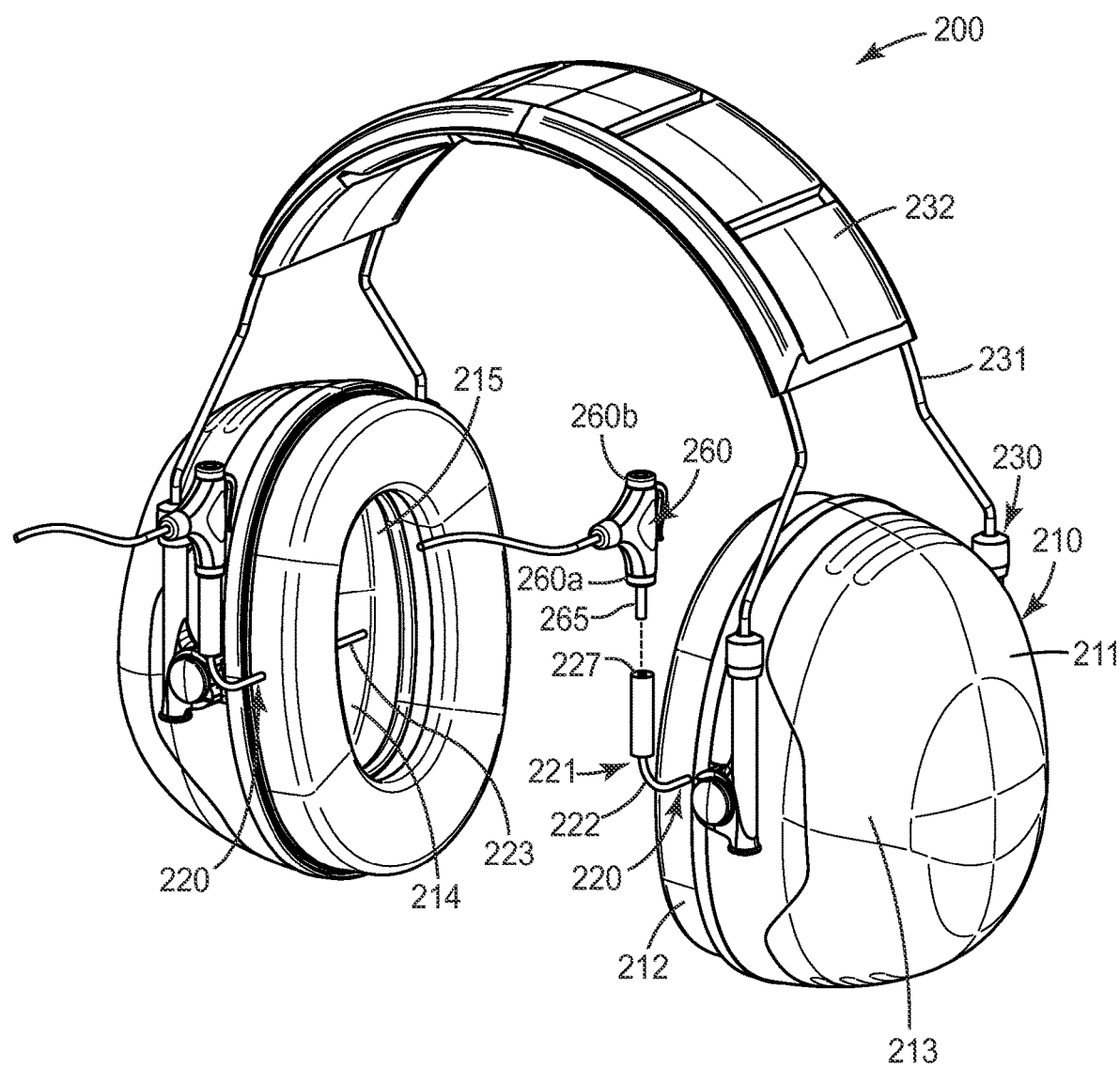
FIG. 2a is a perspective view of an exemplary over-the-ear hearing device according to the present description including an acoustic port extending through a cushion thereof.
Figure 2B:
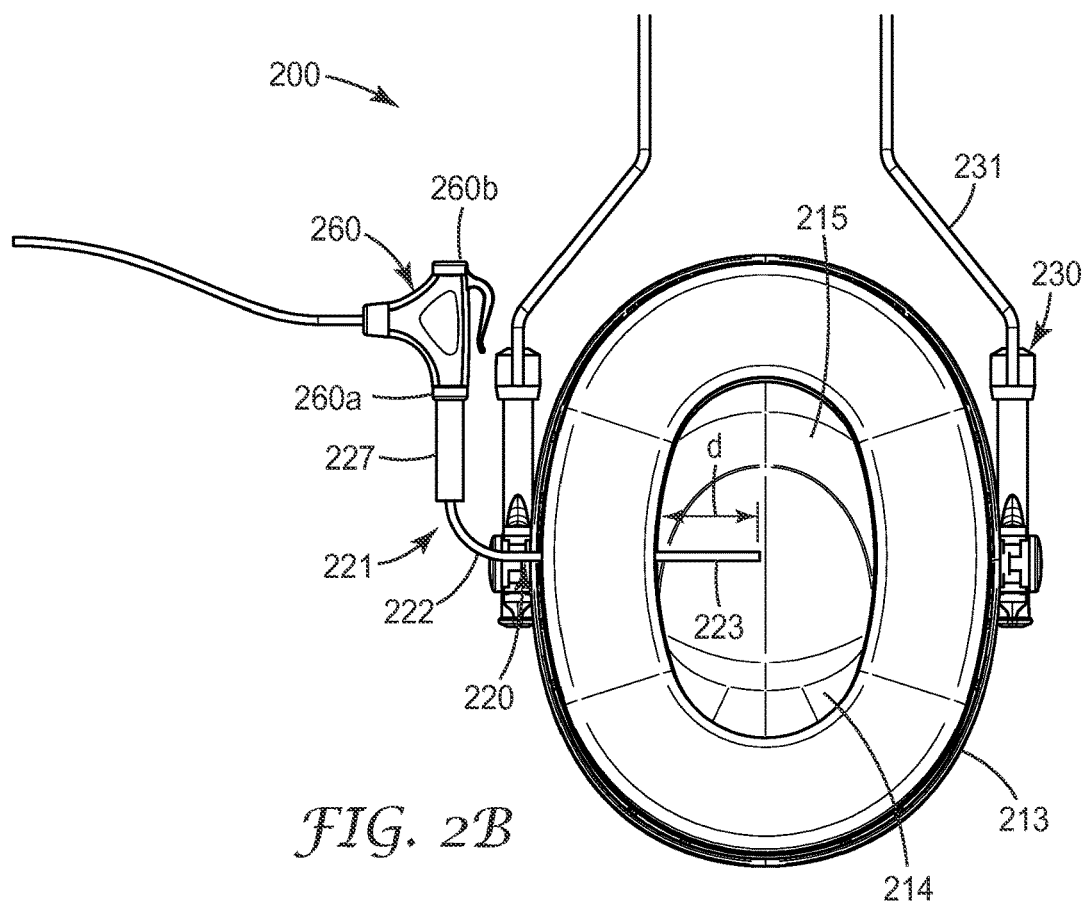
FIG. 2b is a side view of an over-the-ear hearing device according to the present description including an acoustic port extending through a cushion thereof.

FIGS. 2a and 2b show an exemplary over-the-ear hearing device 200 including an ear cup 210 having a shell 211 and a cushion 212, and an attachment portion 230 having an arm 231 and a headband 232. Ear cup 210 is joined to headband 232 by arms 231, and may be supported on the head of a user by headband 232. Ear cup 210 is positioned at least partially over an ear of a user in a position of use. In an exemplary embodiment, cushion 212 forms an acoustic seal with the head of a user to block external sound waves from entering a user's ear canal. Ear cup 210 is generally cup-shaped having an exterior surface 213 and defining an interior volume 214. In an exemplary embodiment, a user's outer ear may generally reside in the interior volume 214 when over-the-ear hearing device 200 is positioned for use, and cushion 212 at least partially encircles the ear of a user.

In an exemplary embodiment, ear cup 210 is a sound attenuating ear cup and includes an acoustic attenuating material 215 that dampens sound waves and/or prevents sound waves from entering interior volume 214. For example, ear cup 210 may include a gas filled cellular material positioned within ear cup 210 and having suitable mechanical stiffness and formability. Such materials include cellular foams such as open cell foams, closed cell foams, slow recovery resilient foams, instantaneous recovery foams, other suitable materials and combinations thereof. In some exemplary embodiments, shell 211 is formed from an acoustic attenuating material such that no additional material or component is positioned within shell 211. Shell 211 may be formed from any suitable material including acrylonitrile butadiene styrene (ABS), polypropylene other suitable materials, and combinations thereof, for example.

Over-the-ear hearing device 200 includes a cushion 212 attached to shell 211. In an exemplary embodiment, cushion 212 forms an acoustic seal around an ear of a user and reduces pressure exerted by hearing device 100 against the user's head to promote comfort. In various exemplary embodiments, cushion 212 exhibits a generally round, oval, rectangular, or other suitable shape defining an opening 212a. In an exemplary embodiment, cushion 212 includes a mating feature the may be joined to a complementary mating feature of shell 211. For example, shell 211 and cushion 212 may include complementary flanges, surfaces, snap-fit components, or other features such that cushion 212 is releasably attachable to shell 211. In other exemplary embodiments, cushion 212 is permanently attached to shell 211 such that cushion 212 cannot be removed from shell 211 without damaging one or both components or cannot be readily reattached. Alternatively or in addition, shell 211 and cushion 212 may be joined with an adhesive or other suitable technique as known in the art. In some exemplary embodiments, cushion 212 is an integral component of ear cup 210 along with shell 211, and, for example, may be formed simultaneously with shell 211.

Cushion 212 is formed from a compliant or flexible material to promote comfortable contact with a user. In an exemplary embodiment, cushion 212 is formed from a cellular material, such as those set forth above, or other suitable cellular materials as known in the art. In various exemplary embodiments, cushion 212 includes an integral skin or a covering such as a cover, a layer, a film, a coating, and/or combinations thereof. A skin or covering may protect the integrity of the foam, inhibit soiling of the foam, promote comfort, and/or enhance the ability to clean the cushion. The covering can also provide aesthetic appeal to the cushion by providing desirable texture and/or color, for example.

Exemplary headband 230 is generally "U-shaped" and sufficiently resilient to fit to the head of a user. In an exemplary embodiment, recovery forces generated in the strained headband when positioned on the head of a user bias the earmuffs inwardly against the user's head and promote secure attachment and acoustic sealing of cushion 212 to the user's head. In other exemplary embodiments, ear cup 210 may be attached to a helmet or other head covering, or supported by other suitable bands passing around a rear of a user's head, as known in the art.

Over-the-ear hearing device 200 includes an acoustic port 220 passing between an exterior and an interior volume 214 of ear cup 210. In an exemplary embodiment, acoustic port 220 provides a sound passageway in fluid communication with an interior volume 214 of ear cup 210 and allows acoustic access to interior volume 214 such that an interior sound level may be detected while ear cup 210 is in a position of use on a user. In various exemplary embodiments, sound passageway of acoustic port 220 may be selectively open and closed, for example by a repositionable cap, plug, switch, elastomeric gasket, or other suitable technique. In some exemplary embodiments, acoustic port 220 is self-closing as described further herein. Acoustic port 220 may be positioned in any suitable location on ear cup 210, and for example, may comprises a passageway through shell 211, cushion 212, between shell 211 and cushion 212 or at other suitable locations.

Acoustic port 220 may be provided with any suitable technique or component such that a microphone component may be sealingly engaged with acoustic port 220, for example. In an exemplary embodiment, acoustic port 220 comprises a tube 221 through ear cup 210. Tube may be an integrally formed with a portion of ear cup 210, such as shell 211 or cushion 212, or drilled or otherwise formed into a portion of ear cup 210. In another exemplary embodiment, tube 221 is a non-integrally formed component passing through shell 211 or cushion 212, through an opening in cushion 212, for example.

Tube 221 includes a proximal end portion 222 proximate an exterior of ear cup 210 and a distal end portion 223 proximate and/or extending into interior volume 214 of ear cup 210. Distal end portion 223 is in fluid communication with interior of ear cup 210 such that sound waves may travel through a passageway defined by tube 221 while ear cup 210 is positioned for use on a user. In some exemplary embodiments, distal end portion 223 extends into an interior of ear cup 210 such that a distance (d) separates distal end portion 223 and a location 219 of ear cup 210 where tube 221 enters interior volume 214, such as an interior surface of shell 211, cushion 212, attenuating material 215, or other portion of ear cup 210. Tube 221 is formed of a shape-stable and/or flexible material such that distal end portion 223 may be positioned and maintained at a desired location in interior volume 214, for example at a location proximate an ear canal of a user. In various exemplary embodiments, distance (d) is between approximately 10 mm and 30 mm, 15 mm and 25 mm, or about 20 mm. Such distances allow distal end portion 223 to be positioned generally at a middle location in interior volume 214, and/or positioned adjacent an entry to a user's ear canal. In other exemplary embodiments, distal end portion 223 may be proximate the interior surface and does not extend inwardly or only extends a small distance into interior of ear cup 210 such that distance (d) is between 0 and 2 mm, for example.

Over-the-ear hearing device 200 is configured to receive a microphone or other suitable instrument for detecting a sound level. In an exemplary embodiment, acoustic port 220 includes an opening, receptacle, protrusion, complementary shape and/or one or more other suitable features that may receive or attach to a microphone. For example, proximal end portion 222 of tube 221 is sized to receive and/or be received by a microphone 260 such that microphone 260 is in fluid communication with interior volume 214 of ear cup 210 through the passageway defined by tube 221. In an exemplary embodiment, proximal end portion 222 is formed from a compliant material such that a part or all of microphone 260, such as a microphone probe or inlet extension 265, may be inserted into and frictionally retained in an enlarged opening 227 at proximal end 222. In other exemplary embodiments, microphone 260 includes an attachment opening or receptacle into which proximal end portion 222 of tube 221 may be inserted.

In an exemplary embodiment, microphone 260 and tube 221 are sealingly engagable. That is, in an exemplary embodiment, an acoustic seal is formed between microphone 260 and tube 221 such that a microphone is in fluid communication with an interior volume 214 of ear cup 210 but not in fluid communication with an exterior of ear cup 210. In some exemplary embodiments, microphone 260, or a component of microphone 260, may be positioned partially or completely in tube 221 proximate distal end portion 223. When in fluid communication with tube 221, microphone 260 may be used to detect a sound level associated with a sound level at interior volume 214 of ear cup 210 while over-the-ear hearing device is in a position of use, as described further herein.

In some exemplary embodiments, microphone 260 may include first and second microphones 260a, 260b, such that first microphone 260a is in fluid communication with acoustic port 220 of over-the-ear hearing device 200 to detect an interior sound pressure level and a second microphone 260b is in fluid communication with an exterior sound pressure level proximate over-the-ear hearing device 200. For example, first and second microphones may be joined, share a common housing and/or be arranged in a back-to-back relative configuration.

Figure 3:
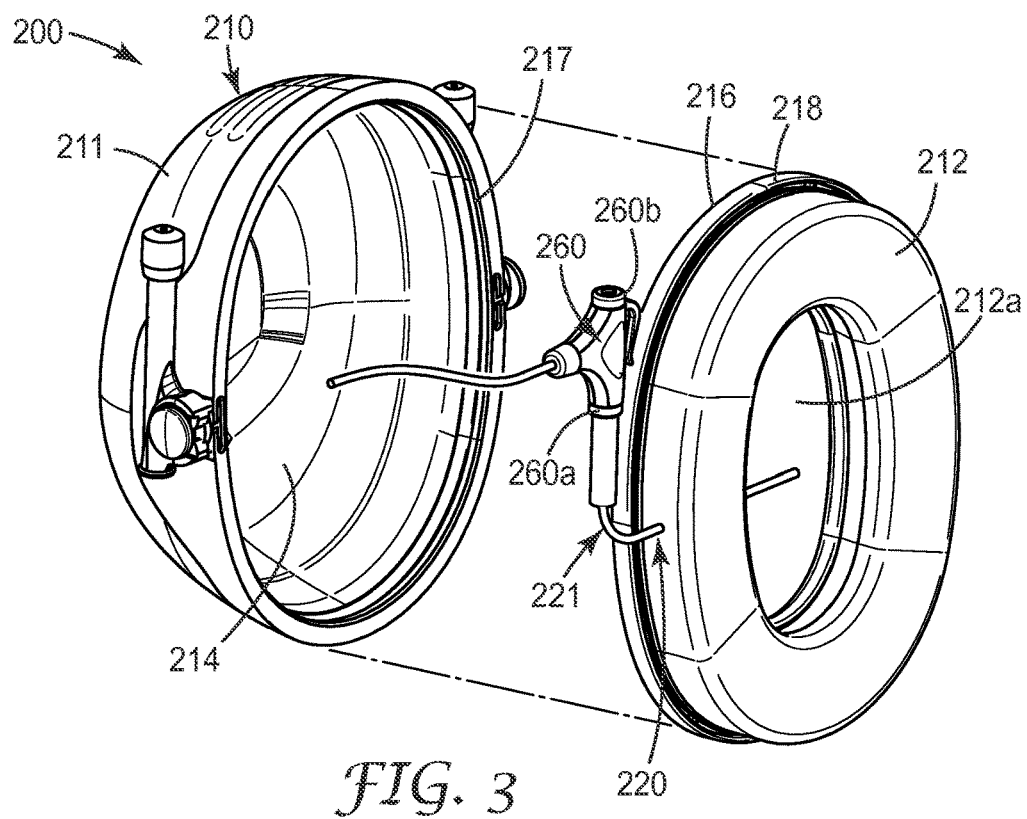
FIG. 3 is a partial exploded view of an exemplary ear cup including a cushion having an acoustic port according to the present description.

FIG. 3 shows a partial exploded view of over-the-ear hearing device 200 including ear cup 210 having a shell 211 and a first cushion 212. As described above, exemplary first cushion 212 includes an acoustic port 220 that provides a sound passageway in fluid communication with an interior volume 214 of ear cup 210 when assembled. In an exemplary embodiment, first cushion 212 is removably attachable to shell 211 to provide an over-the-ear hearing device 200 that may be positioned at least partially over the ear of a user when assembled. For example, cushion 212, or a component attached to cushion 212 may include an attachment ring 218 having a mating feature 216 that may be joined to a complementary mating feature 217 of shell 211. In this way, first cushion 212 is interchangeable with one or more second cushions, as desired by a user. Over-the-ear hearing device 200 may include a second cushion (not shown) attachable to shell 211 when over-the-ear hearing device 200 is used for a particular purpose, such as providing a desired level of hearing protection in a noisy environment. Second cushion may be replaced by first cushion 212 as desired to perform an acoustic assessment of over-the-ear hearing device 200.

A removably attachable cushion 212 having an acoustic port 220 providing access to interior volume 214 of ear cup 210 allows an acoustic assessment of over-the-ear hearing device 200 to be performed while over-the-ear hearing device 200 is positioned for use at least partially over the ear of a user. A cushion attached to other components of over-the-ear hearing device 200 during normal use is removed and replaced by first cushion 212 having acoustic port 220. A microphone, such as dual microphone 260, is attached to tube 221 of acoustic port 220 such that first microphone 260a is in fluid communication with interior volume 214 of ear cup 210, for example through a passageway defined by tube 221. A second microphone 260b may be positioned to detect a sound level proximate an exterior of over-the-ear hearing device 200. With over-the-ear hearing device 200 in a position of use, over-the-ear hearing device 200 is exposed to at least a first test sound. Acoustic performance of over-the-ear hearing device 200 may be assessed by comparing an interior sound level detected by first microphone 260a via acoustic port 220 and an exterior sound level detected proximate the exterior of over-the-ear hearing device 200 by second microphone 260b.

An over-the-ear hearing device assessment apparatus having an acoustic port 220 extending through a removeably attachable cushion 212 allows acoustic access to interior volume 214 without interfering with a fit of over-the-ear hearing device 200 on a user, for example because no wires or other components are required to pass between cushion 212 and a user's head. Furthermore, an assessment may be performed on the hearing device unit worn by a particular user, outside of a laboratory setting, if desired, and may be performed periodically over the life of the unit simply by attaching cushion 212. Accordingly, an attenuation value, such as a Personal Attenuation Rating (PAR), may be determined that is highly representative of an attenuation experienced by a user when wearing a particular over-the-ear hearing device 200 in the field.

Figure 4A:
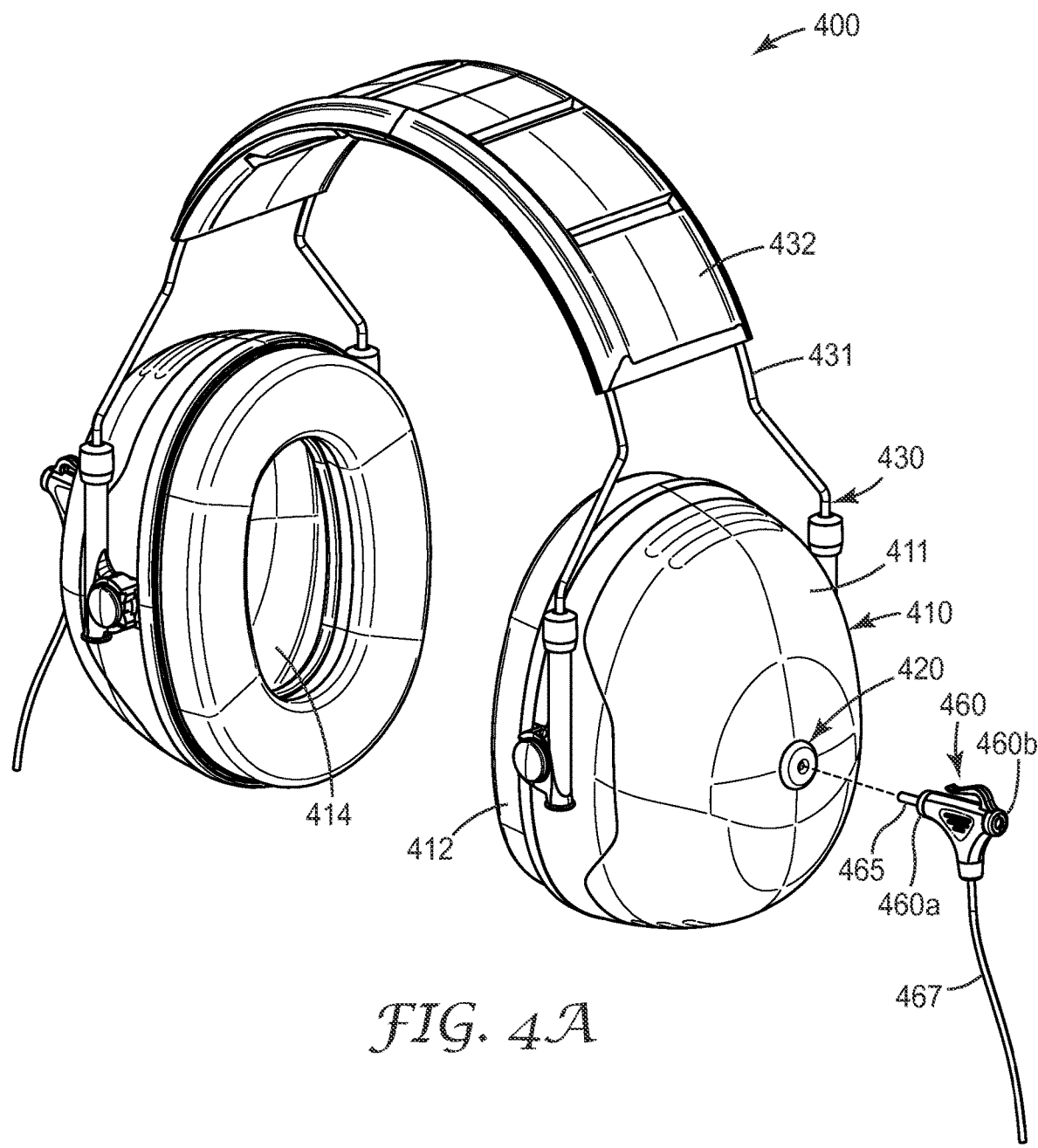
FIG. 4a is a perspective view of an exemplary over-the-ear hearing device according to the present description including an acoustic port extending through a cup portion.
Figure 4B:
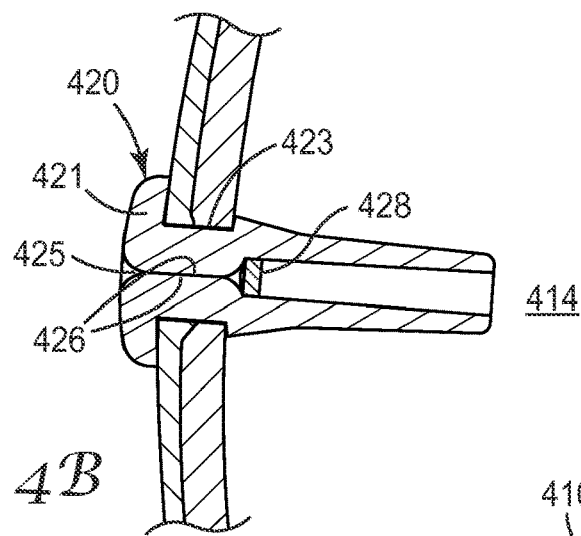
FIG. 4b is a cross-sectional view of an exemplary over-the-ear hearing device according to the present description including an acoustic port extending through a cup portion with the port closed.
Figure 4C:
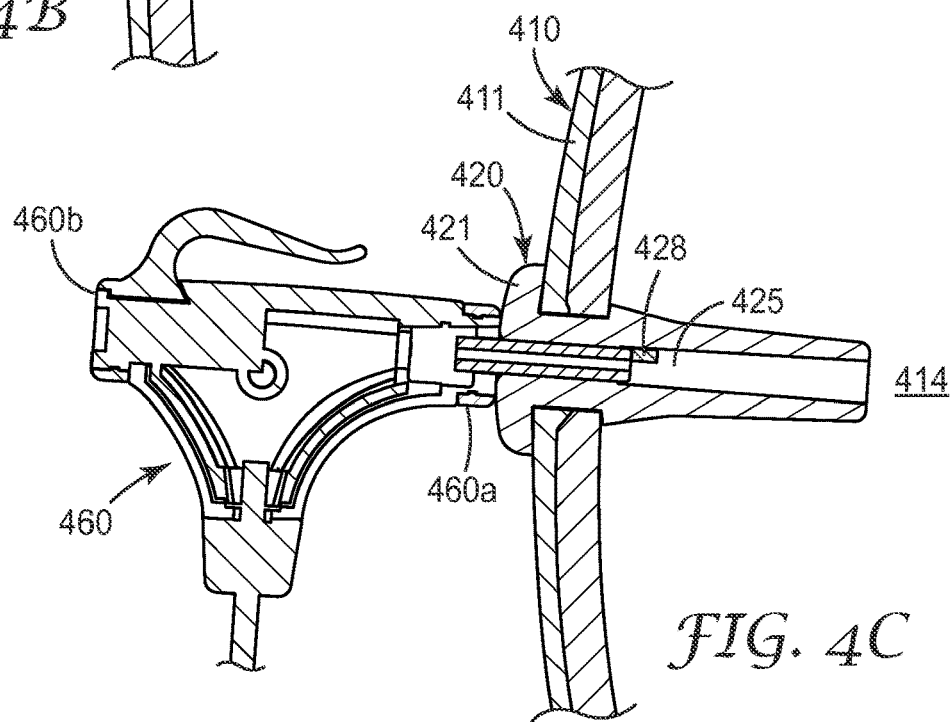
FIG. 4c is a cross-sectional view of an exemplary over-the-ear hearing device according to the present description including an acoustic port extending through a cup portion with the port open and a microphone component extending at least partially therethrough.

FIGS. 4a through 4c show an exemplary over-the-ear hearing protection assessment apparatus including an over-the-ear hearing device 400 and one or more microphones 460. Microphones 460 are operatively connected to a controller and sound source (not shown) for performance of an acoustic assessment, as described above with respect to FIG. 1, for example. In an exemplary embodiment, microphones 460 include a probe or inlet extension 465 providing an extended inlet through which sound waves may enter to be detected by microphone 460. In some exemplary embodiments, microphone 460 may include a wire 467 connected to a controller or other portion of an acoustic assessment apparatus. In other exemplary embodiments, microphone 460 is configured for wireless communication to a controller or other components of the acoustic assessment apparatus.

Over-the-ear device 400 includes an acoustic port 420 that selectively allows acoustic access to an interior volume 414 of device 400 while in a position of use at least partially covering a user's ear. Similar to over-the-ear hearing device 200 described above, device 400 includes an ear cup 410 having a shell 411 and a cushion 412, and an attachment portion 430 having an arm 431 and a headband 432. Ear cup 410 is joined to headband 432 by arms 431, and may be supported on the head of a user by headband 432.

Acoustic port 420 provides a sound passageway 425 in fluid communication with an interior volume 414 of ear cup 410 and allows acoustic access to interior volume 414 such that an interior sound level may be detected while ear cup 410 is in a position of use on a user. In an exemplary embodiment, acoustic port 420 is positioned on an outward facing surface of shell 411. Alternatively or in addition, one or more acoustic ports 420 may be positioned at any suitable location on ear cup 410, and for example, may comprise a passageway through shell 411, cushion 412, between shell 411 and cushion 412 or at any other suitable location where a passageway may be provided between an interior volume 414 and an exterior of hearing device 400.

Acoustic port 420 may be selectively opened and closed such that a passageway 425 may be altered between an open condition in which passageway 425 is blocked and an open condition allowing fluid communication through passageway 425. For example, acoustic port 420 may include a repositionable cap, plug, switch, elastomeric gasket, compressible or resilient feature, or other suitable component that can be manipulated by a user to toggle between an open condition and a closed condition.

Referring to FIGS. 4b and 4c, acoustic port 420 includes a passageway 425 defined by a tube 421. Tube 421 may be positioned in an opening 423 of shell 411, or may be integrally formed with shell 411. In an exemplary embodiment, at least a portion of tube 421 is formed from a compressible or resilient material and retained in opening 423 in sealing engagement with shell 411 and/or one or more other components of ear cup 410. In an exemplary embodiment, acoustic port 420 is self-sealing and includes a material having sufficient resilience to expand and/or flex to block passageway 425 in a closed configuration and to allow sealing engagement with a microphone 460 and/or microphone probe or inlet extension 465 in an open configuration. For example, self-sealing acoustic port 420 may include a gasket, tube, or other component made of a silicon, ethylene propylene diene monomer (EPDM), other suitable resilient material as known in the art, and/or suitable combinations thereof. In one exemplary embodiment, tube 421 includes opposing portions 426 that expand to block tube in a closed configuration and may be compressed to allow sealing engagement with a microphone 460 and/or microphone probe or inlet extension 465 in an open configuration. Alternatively or in addition, an exemplary tube 421 may include a resilient flap 428 biased towards a closed configuration in which flap 428 blocks passageway 425, and movable or flexible such that flap 428 does not block passageway 425 in an open configuration, for example by being pushed out of a closed configuration by a microphone 460 and/or microphone probe or inlet extension 465.

FIG. 4b shows acoustic port 420 in a closed configuration. In an exemplary embodiment, passageway 425 is blocked by opposing portions 426 of tube 421 in an expanded condition and/or in contact with one another to occlude passageway 425 and prevent fluid communication through passageway 425. Acoustic port 420 is acoustically sealed such that the passage of sound waves is substantially prevented when acoustic port 420 is in a closed position. Accordingly, hearing device may be used as desired for a particular purpose, for example to attenuate sound in a noisy environment. No additional manipulation is required of a user to close self-sealing acoustic port 420 before use.

FIG. 4c shows acoustic port in an open configuration. Opposing portions 426 of tube 421 are separated and/or compressed by a microphone 460 inserted into passageway 425. In an exemplary embodiment, microphone 460 includes a probe or inlet extension 465 having a shape complementary to that of acoustic port 420 such that probe 465 may be at least partially inserted into acoustic port 420. Probe 465 has an increased stiffness or rigidity relative to tube 421 such that opposing portions 426 of tube 421 may be caused to be separated or compressed when probe 465 is inserted into acoustic port 465. In an exemplary embodiment, restorative forces of opposing portions 426 of tube 421 press against probe 465 to create an acoustic seal but are insufficient to compress probe 465. With probe 465 inserted in acoustic port 420, microphone 460 is in fluid communication with interior volume 414 of ear cup 410 through passageway 425 but not in fluid communication with an exterior of ear cup 210. In other exemplary embodiments, microphone 460 may be configured such that all or a portion of microphone 460 may be inserted into passageway 425 of tube 421 to separate opposing portions 426 and allow fluid communication between interior volume 414 and microphone 460.

Figure 4D:
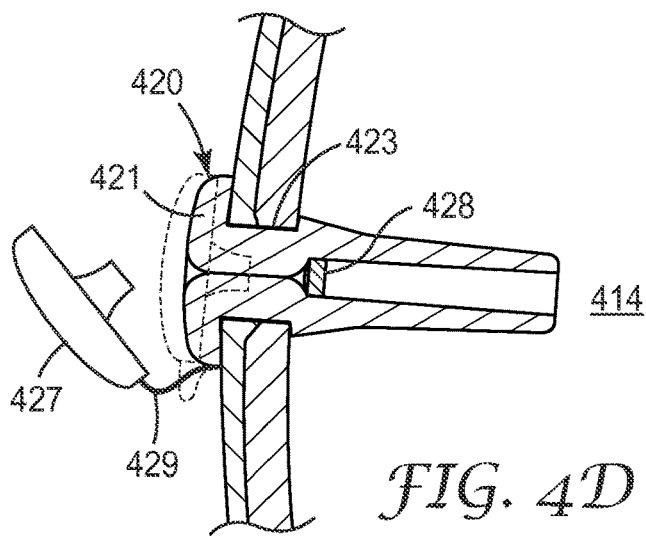
FIG. 4d is a cross-sectional view of an exemplary over-the-ear hearing device according to the present description including an acoustic port having a repositionable cap.

In an exemplary embodiment shown in FIG. 4d, acoustic port 420 includes a repositionable cap 427 that may be manual inserted to provide a closed configuration. Repositionable cap 427 is attached to acoustic port 420 and/or ear cup 410 by a flexible tether 429 such that repositionable cap 427 remains attached to over-the-ear device 400 even when not blocking acoustic port 420. Repositionable cap may be provided as an alternative, or in addition to, other features of an exemplary acoustic port as described herein to selectively block passage of sound through acoustic port 420 and/or to prevent entry or contamination from unwanted debris.

In an exemplary embodiment, interior volume 414 is not in fluid communication with the exterior in both a closed configuration and an open configuration in which microphone 460 or probe 465 is positioned in acoustic port 420 because microphone 460 and/or probe 465 is sealingly engaged with tube 421. When microphone 460 and/or probe 465 is sealingly engaged with tube 421, an acoustic seal is formed between acoustic port 420 and microphone 460 and/or probe 465 (e.g. due to restorative forces of opposing portions 426 of tube 421). In this way, passageway 425 remains out of fluid communication with an exterior of over-the-ear device 400 in both open and closed configurations when device 400 is in a position of use, and sound waves are prevented from entering interior volume 414 of ear cup 410 whether acoustic port 420 is in an open or a closed configuration. In an exemplary embodiment, an acoustic attenuation provided by hearing device 400 is substantially the same whether acoustic port 420 is in a closed position or in an open position with microphone 460 positioned therein. Accordingly, an acoustic assessment as described herein provides a highly representative determination of an attenuation provided by hearing device 400. While prior methods of testing performance of ear muffs, for example, may involve positioning a wired microphone between a cushion and a users head, and thus altering the a seal that may otherwise be achieved between the ear cup and a user's head, a test may be performed while device 400 is in a normal position of use.

Self-sealing port 420 allows an acoustic assessment of over-the-ear device 400 to be performed while device 400 is positioned for use at least partially over the ear of a user. First microphone 460a and/or probe or inlet extension 465 is sealingly engaged with acoustic port 420 such that microphone 460 is in fluid communication with interior volume 414 of ear cup 410, for example through passageway 425. A second microphone 460b may be positioned to detect a sound level proximate an exterior of device 400. With device 400 in a position of use, device 400 is exposed to at least a first test sound. Acoustic performance may be determined by comparing an interior sound level detected by first microphone 460a via acoustic port 420 and an exterior sound level detected proximate the exterior of device 400 by second microphone 460b.

Over-the-ear devices and over-the-ear hearing protection assessment apparatuses as described herein provide several features and advantages that facilitate accurate and repeatable acoustic assessment of over-the-ear devices. The presence of an acoustic port passing through the over-the-ear device allows acoustic access to an interior volume without altering the normal fit of the device when in a position of use. That is, there are no wires or other components passing between the device and a user's head that could interfere with proper fit of the device or otherwise allow undesirable passage of sound into the interior volume. Furthermore, an acoustic port as described herein allows acoustic assessment of an over-the-ear device unit to be worn by a user in the field, and allows testing of that particular unit over the life of the unit. In this way, an attenuation value, such as a Personal Attenuation Rating (PAR), may be determined that is highly representative of an actual attenuation experienced by a user when wearing the over-the-ear device in the field, and a test may be repeated to verify a desired attenuation continues to be provided over the life of the unit.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the exact details and structures described herein, but rather by the structures described by the language of the claims, and the equivalents of those structures. Any patent literature cited herein is hereby incorporated herein by reference in its entirety to the extent that it does not conflict with the description presented herein.

Any feature or characteristic described with respect to any of the above embodiments can be incorporated individually or in combination with any other feature or characteristic, and are presented in the above order and combinations for clarity only. That is, the present disclosure contemplates all possible combinations and arrangements of various features of each of the exemplary embodiments and components described herein, and each component may be combined or used in conjunction with any other component as may be desired for a particular application.

What is claimed is:

1. An over-the-ear hearing assessment device, comprising:
    an ear cup defining an interior volume and configured to be positioned at least partially over an ear of a user, the ear cup including a shell, a cushion and an acoustic port extending through the cushion, from an exterior to the interior volume of the ear cup;
    wherein the acoustic port comprises a first mating feature sealingly engagable with a microphone, wherein the microphone is configured to receive a sound level within the interior volume.

2. The device of claim 1, wherein the acoustic port passes through the shell of the ear cup.

3. The device of claim 1, wherein the acoustic port is self-sealing.

4. The device of claim 1, wherein the acoustic port comprises a tube extending through the ear cup.

5. The device of claim 4, wherein the tube comprises a distal end proximate the interior volume of the ear cup, and the tube extends a distance (d) into the interior volume.

6. The device of claim 1, wherein the cushion is removably attachable to the shell.

7. The device of claim 1, wherein the microphone is a first microphone, wherein the microphone includes a second complementary mating feature, and the microphone and the acoustic port are attachable at the first and second complementary mating features.

8. The device of claim 7, further comprising a second microphone configured to detect an exterior sound level.

9. The device of claim 7, wherein the first and second microphones share a common housing.

10. A method of evaluating performance of an over-the-ear device, comprising:
    positioning an over-the-ear hearing device in a position of use over at least one ear of a user, the over-the-ear hearing device comprising an ear cup defining an interior volume and comprising a shell, a cushion, and an acoustic port extending through the cushion, from an exterior to the interior volume of the ear cup;
    exposing the hearing device to at least one test sound;
    detecting a sound, through the acoustic port, using a microphone, wherein the detected sound is an interior sound level detected in the interior volume and wherein the microphone is in fluid communication with the acoustic port;
    comparing the detected interior sound level with an exterior sound level detected proximate the exterior of the hearing device.

11. The method claim 10, wherein the acoustic port passes through the shell of the ear cup.

12. The method of claim 10, wherein the acoustic port is self-sealing.

13. The method of claim 10, wherein the acoustic port comprises a tube extending through the ear cup.

14. The method claim 13, wherein the tube comprises a distal end proximate the interior volume of the ear cup, and the tube extends a distance (d) into the interior volume.

15. The method of claim 10, wherein the cushion is removably attachable to the shell.

16. The method of claim 10, further comprising positioning a first microphone in sealing engagement with the acoustic port configured to detect the interior sound level.

17. The method of claim 16, further comprising positioning a second microphone proximate an exterior of the over-the-ear hearing device.

18. The method of claim 17, wherein the first and second microphones share a common housing.

19. The method of claim 10, wherein the cushion comprises cellular foam, and the acoustic port extends through the cellular foam.

* * * * *